United States Patent [19]
Fujita

[11] Patent Number: 4,575,337
[45] Date of Patent: Mar. 11, 1986

[54] ORTHODONTIC APPLIANCE

[76] Inventor: Kinya Fujita, No. 3998-5, Kamariya-cho, Kanazawa-ku, Yokohama-shi, Kanagawa-ken, Japan

[21] Appl. No.: 555,068

[22] Filed: Nov. 25, 1983

[30] Foreign Application Priority Data

Nov. 25, 1982 [JP] Japan .................... 57-178070[U]

[51] Int. Cl.⁴ .............................................. A61C 7/00
[52] U.S. Cl. ......................................... 433/8; 433/15
[58] Field of Search .................. 433/16, 8, 9, 11, 15

[56] References Cited

U.S. PATENT DOCUMENTS

| | | | |
|---|---|---|---|
| 3,775,850 | 12/1973 | Northcutt | 433/9 |
| 4,139,945 | 2/1979 | Di Giulio | 433/16 |
| 4,209,906 | 7/1980 | Fujita . | |
| 4,337,037 | 6/1982 | Korz | 433/8 |
| 4,354,833 | 10/1982 | Fujita . | |
| 4,355,975 | 10/1982 | Fujita | 433/11 |

Primary Examiner—Robert Peshock
Attorney, Agent, or Firm—Lowe, King, Price & Becker

[57] ABSTRACT

The present invention relates to an orthodontic appliance to treat irregularities of teeth by attaching an arch wire holder to a plurality of teeth and then connecting one or more orthodontic wires to the arch wire holders. The bracket constituting an arch wire holder is provided with an arch wire fixing slot formed with a specified radius of curvature approximately conforming to the diameter of the arch wire. The curvature radius of the arch wire fixing slot is determined by the purpose of application, namely, it depends on whether it attaches onto the outside (buccal side) surface or the inside (lingual side) surface of the teeth, and for which teeth it is employed. This arch wire holder is especially effective when the bracket is attached to the inside of the teeth for orthodontic purposes, for it then allows the application of corrective forces on the teeth without being easily visible in the user's mouth.

11 Claims, 18 Drawing Figures

ORTHODONTIC APPLIANCE

BACKGROUND OF THE INVENTION

This invention relates to an orthodontic appliance to treat malocclusion, and particularly to the improvement of an arch wire holder attached to a user's teeth in order to hold an orthodontic arch wire thereat.

FIG. 1 illustrates the newest advanced technique for the treatment of malocclusion. As illustrated, brackets (1) constituting the arch wire holders are fixed to teeth $(2_{11})$, $(2_{12})$, ... $(2_{17})$, and one or more orthodontic wires (3) are inserted into these brackets (1) and are fixed therein. The malocclusion is corrected forces applied to the subject teeth by elasticity of the arch wire (3). For example, as shown in FIG. 2, when the central incisors $(2_{11})$ are protruding outward, as shown by solid lines, and are to be corrected to have normal occlusion, as shown by broken lines, bands (4) are attached to teeth $(2_{11})$ and brackets (1) are bonded to these bands (4) as illustrated in FIG. 1. Then one curved orthodontic arch wire (3) is fixed to these brackets (1), and its elasticity is used to apply corrective forces to the teeth for the treatment.

The major disadvantage of this method is that, since the brackets (1) are attached to the outside (buccal side) surface of the teeth $(2_{11})$, brackets (1) are exposed when the patient opens his mouth, affecting his facial appearance. To solve this problem, the present applicant has already proposed an appliance, disclosed in U.S. Pat. Nos. 4,209,906 and 4,354,833), in which all brackets (1) are fixed inside (lingual side) surface the teeth $(2_{11})$, $(2_{12})$, ... $(2_{17})$ as shown in FIG. 3, and arch wire (3) is put in the slots of these brackets. This makes the brackets (1) and arch wire (3) invisible even when the user's mouth is opened, and greatly reduces the mental burden of the patient.

Both in the conventional method (FIG. 1) and new method (FIG. 3), the envelope linking the teeth is almost elliptical.

However, in the conventional brackets (1) shown in FIG. 1, the arch wire fixing slot (5) was straight, making it difficult to insert therein an arch wire (3) which was curved in advance. The wire here has to be curved and adjusted for each bracket. This requires a considerable amount of the dentist's time and causes the originally carefully bent arch wire to be deformed.

BRIEF SUMMARY OF THE INVENTION

An object of the present invention is to provide an arch wire holder which permits smooth insertion of an arch wire into an arch wire fixing slot. To achieve this purpose, the arch wire fixing slot is formed with a specified radius of curvature approximately conforming to the diameter of the arch wire. This makes it possible to insert the arch wire into the fixing slot almost without wire deformation, ensuring easy operation and accurate treatment by the dentist.

Another object of this invention is to provide an effective means for orthodontic treatment by fixing the arch wire holder to the inside surface of the teeth. To achieve this purpose, in the present invention, the flange contacting the teeth is made slightly bent in conformity to the shape of the lingual side surface of the teeth, and the arch wire fixing slots formed on a bracket are not only necessarily parallel to the tooth axis, but are tilted by the specified angle with respect to the tooth axis to ensure easy insertion of the arch wire. This ensures easy insertion of the wire into the arch wire holder fixed on other teeth, even after both ends of the arch wire are fixed to the molars.

Other purposes and advantages of the present invention will be clarified in the following description using the attached drawings.

DETAILED DESCRIPTION

Figure 5:
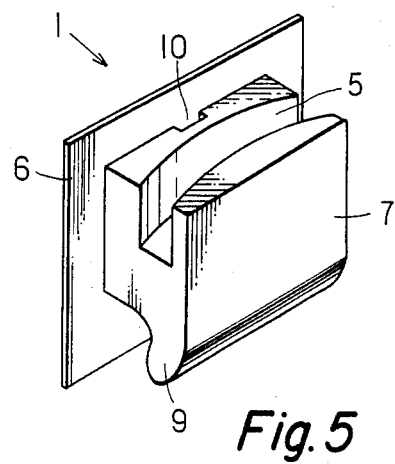
FIGS. 5 and 6 are oblique and plan views, respectively, of an arch wire holder, respectively.

The following describes the embodiments of the present invention as illustrated in FIGS. 5 to 10. In FIGS. 5 (a) and (b), arch wire holder (1) consists of a flange (6), which in use is directly bonded to the tooth, and a bracket (7) installed on this flange (6). This bracket (7) is provided with a bent arch wire fixing slot (5).

Figure 1:
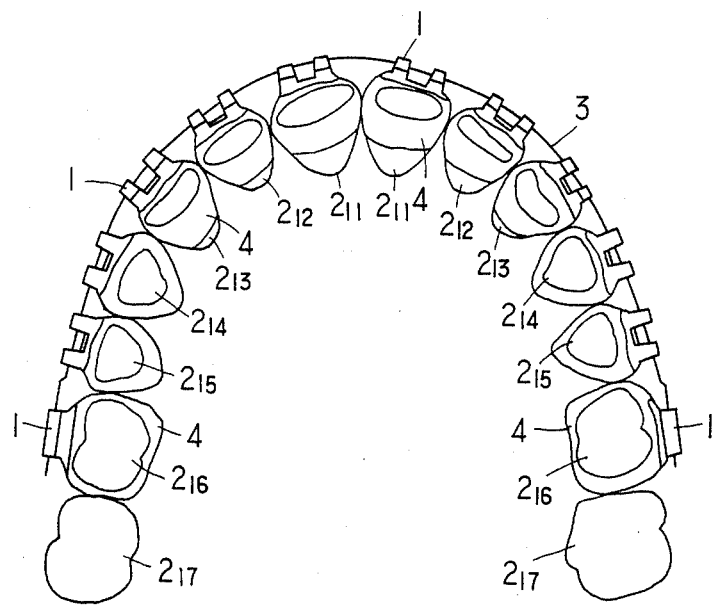
FIG. 1 is an illustration of the orthodontic treatment technique in which the brackets constituting the arch wire holder are attached to the outside (buccal side) surfaces of the teeth.
Figure 2:
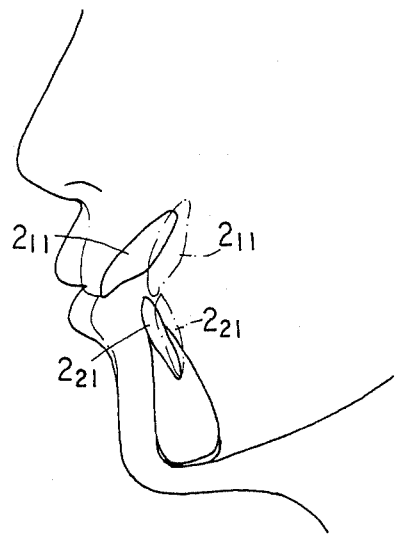
FIG. 2 illustrates the states of teeth before and after the orthodontic treatment.

The above-mentioned flange (6) may be a band (4), as illustrated in FIG. 1, or may be integral with the base (tooth side) of the bracket (7).

Figure 3:
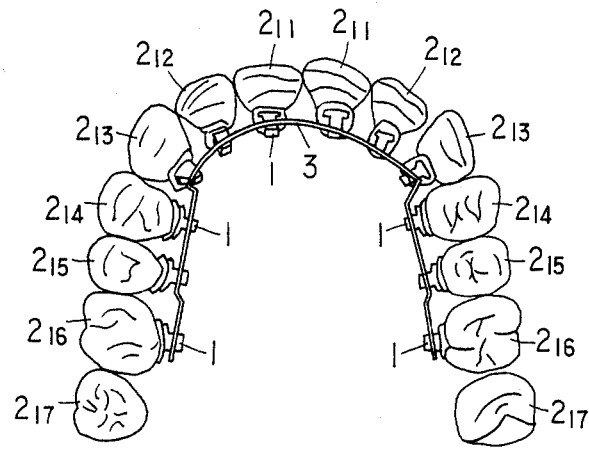
FIG. 3 is an illustration of the orthodontic treatment technique in which the brackets constituting the arch wire holder are attached to the inside (lungual side) surface of the teeth.
Figure 4:
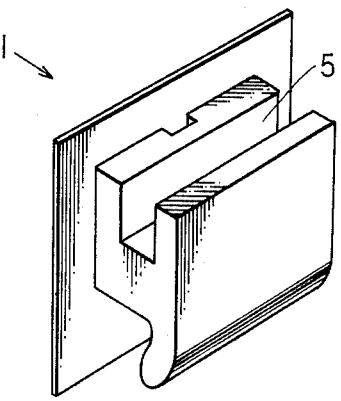
FIG. 4 is an oblique view of a conventional bracket.

The following describes the case where the flange (6) comprising the bonding plate is employed. In FIG. 5, the top surface of bracket (7) is provided with the previously-curved arch wire fixing slot (5) having the specified radius of curvature (R). This radius of curvature (R) can be set, for example, from 2 mm to an infinite value, to meet a variety of application requirements, depending on (a) whether the appliance is bonded to the outside surface of the teeth as shown in FIG. 1, or inside surface of the teeth as shown in FIG. 3; (b) which teeth the appliance is attached to (upper or lower jaw, large jaw or small jaw); (c) the state of teeth alignment and (d) whether the teeth (such as canine teeth) protrude outward even at normal occlusion. It should be noted that, in FIGS. 5 (a) and (b), the lower projection (9) of bracket (7) and inner vertical groove (10) is formed to attach an auxiliary wire, rubber ring or ligature wire.

Figure 6:
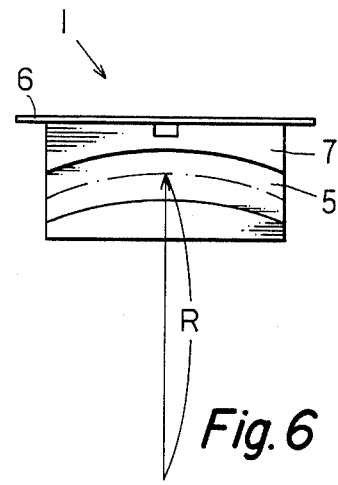
Figure 7:
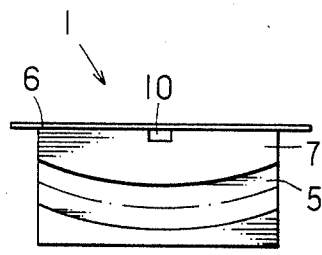
FIGS. 7 and 8 are plan and side views of the other embodiments of the present invention.
Figure 8:
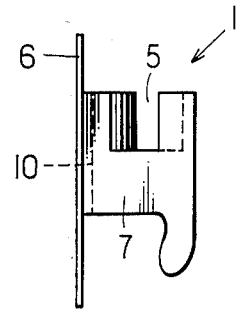

When the arch wire holder (1) is attached to the inside surface of the teeth as in FIG. 3, the arch wire fixing slot (5) is usually curved away from the flange (6) as illustrated in FIGS. 5 and 6. When the arch wire holder (1) is attached to the outside surface of the teeth as in FIG. 1, the slot is usually curved toward the flange (6), as illustrated in FIGS. 7 and 8.

Figure 9:
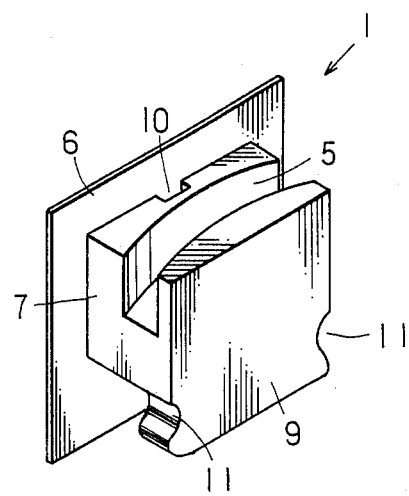
FIG. 9 is an oblique view of one embodiment of the present invention.

In FIG. 9, a neck (11) is formed on the said lower projection (9) to facilitate attachment of a rubber ring.

Figure 10:
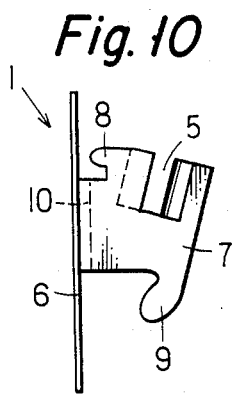
FIGS. 10 through 14 are side views of still further embodiments of the arch wire holder of this invention.
Figure 11:
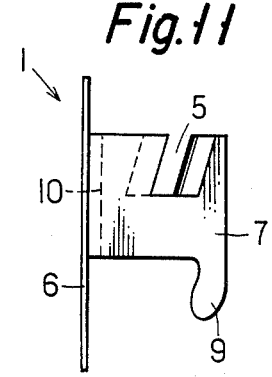
Figure 12:
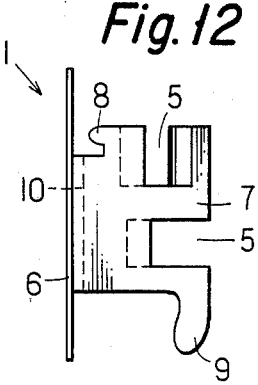
Figure 13:
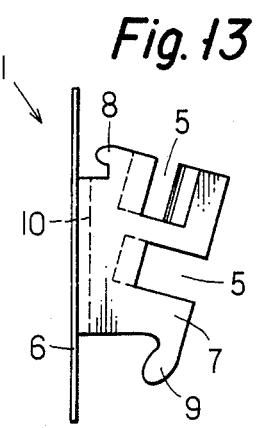
Figure 14:
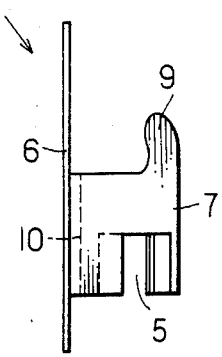

FIGS. 10 through 13 illustrate application examples using different geometries for brackets (7). In FIG. 10, the wire fixing slot (5) is tilted with respect to the tooth axis, and upper and lower projections (8) and (9) are provided. In FIG. 11, the arch wire fixing slot (5) is tilted with respect to the tooth axis, and a lower projection 9 is provided. In FIG. 12, the arch wire fixing slot (12) perpendicular to the tooth axis and the arch wire fixing slot (5) parallel to the tooth axis are provided on the top and side, respectively and the upper and lower projections (8) and (9) are provided also, as shown. In this case, the arch wire fixing slot parallel to the tooth axis may be curved at the bottom. In FIG. 13, the arch wire fixing slots (5) on the top and (12) at the side are tilted with respect to the tooth axis. In this case, the arch wire fixing slot (5) on the side may be curved at the bottom. The tilt may be downward, upward or horizontal. In FIG. 14, the arch wire fixing slot (5) is formed on the lower surface.

Figure 15:
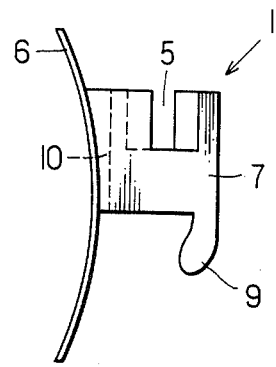
FIGS. 15 and 16 are plan views of further embodiments of the invention using different flanges.
Figure 16:
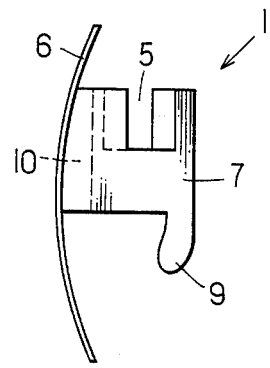
Figure 17:
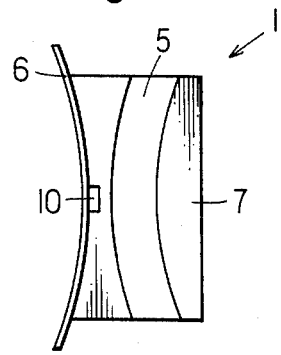
FIGS. 17 and 18 are also plan views of further embodiments of the invention using different flanges.
Figure 18:
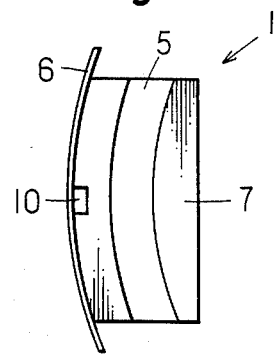

FIGS. 15 through 18 show other application examples of the flange (6). FIGS. 15 and 16 show the flange bent curved in the opposite or same side of the bracket (7), when viewed from the side. FIGS. 17 and 18 show the flange curved in the opposite or same side of the bracket (7) viewed from above. Furthermore, the flange can be curved in three dimensions, with the combinations of FIGS. 15 through 18, depending on the shape of the teeth or purpose of the application.

The shapes of the bracket (7) and flange (6) are not limited only to the application examples given above.

What I claim is:

1. An orthodontic appliance for applying forces to correct malocclusion of teeth, comprising:
   a generally U-shaped orthodontic first curved arch wire for applying said corrective forces;
   a plurality of arch wire support brackets cooperating with and supporting in a predetermined manner said arch wire, each of said brackets being attachable to individual teeth at either the buccal or lingual side thereof, a laterally central portion of a width of each of said brackets being substantially aligned with respect to a laterally central portion of the attached buccal or lingual side, respectively, of said attached tooth;
   at least one of said brackets being formed with a curved arch wire engaging a first slot extending the full width thereof, said first slot being curved to match the shape of a corresponding portion of said curved arch wire engaged into corresponding slots of adjacent support brackets attached to a plurality of said teeth; and
   said first slot is curved to be concave toward an end surface of said bracket with which said bracket is attached to a tooth.

2. An orthodontic appliance for applying forces to correct malocclusion of teeth, comprising:
   a generally U-shaped orthodontic first curved arch wire for applying said corrective forces;
   a plurality of arch wire support brackets cooperating with and supporting in a predetermined manner said arch wire, each of said brackets being attachable to individual teeth at either the buccal or lingual side thereof, a laterally central portion of a width of each of said brackets being substantially aligned with respect to a laterally central portion of the attached tooth;
   at least one of said brackets being formed with a curved arch wire engaging a first slot extending the full width thereof, said first slot being curved to match the shape of a corresponding portion of said curved arch wire engaged into corresponding slots of adjacent support brackets attached to a plurality of said teeth;
   a generally U-shaped orthodontic second curved arch wire for applying said corrective forces; and
   in at least one of said slotted brackets, adjacent and substantially normal to said first slot therein, a second slot for engaging said second arch wire, also extending the full width of that bracket into which said first and said second slots are formed.

3. An orthodontic appliance according to claim 2, wherein:
   said second slot is defined by two substantially parallel flat surfaces substantially normal to said side wall surfaces of said first slot and a cylindrically arcuate bottom wall surface substantially parallel to said side surfaces of said first slot.

4. An orthodontic appliance according to claim 3, wherein:
   said first slot is defined by two substantially parallel convex and concave side wall surfaces and an arcuate bottom wall surface.

5. An orthodontic appliance according to claim 3, wherein:
   said convex and concave side wall surfaces of said first slot are so arranged as to each be generated by a straight line generatrix moved substantially in parallel to an end surface of said bracket with which said bracket is attached to a tooth.

6. An orthodontic appliance according to claim 3, wherein:
   said convex and concave side wall surfaces of said first slot are so arranged as to each be generated by a straight line generatrix moved with a constant inclination relative to an end surface of said bracket with which said bracket is attached to a tooth.

7. An orthodontic appliance according to claim 3, wherein:
   said first slot is curved to be convex toward an end surface of said bracket with which said bracket is attached to a tooth.

8. An orthodontic appliance according to claim 3, wherein:
   said first slot is curved to be concave toward an end surface of said bracket with which said bracket is attached to a tooth.

9. An orthodontic appliance for applying forces to correct malocclusion of teeth, comprising:
   a generally U-shaped orthodontic arch wire bent to a predetermined curve for applying said corrective forces to selected teeth;
   a plurality of arch wire support brackets cooperating with and supporting in a predetermined manner said arch wire, each of said brackets being attachable to individual ones of said selected teeth on the lingual side thereof, a laterally central portion of a width of each of said brackets being substantially aligned with respect to a laterally central portion of said lingual side of said attached tooth;
   at least one of said brackets being formed with a curved first slot extending the full width thereof such that said first slot is defined by two substantially parallel surfaces curved to be concave toward an end surface of said bracket with said bracket attached to said tooth and an arcuate bottom wall surface substantially normal to said parallel curved surfaces, and formed also to have a curved second slot extending the full width thereof such that said second slot is defined by two substantially parallel planar surfaces oriented substantially parallel to said arcuate bottom surface of said first slot and a cylindrical curved surface substantially normal to said parallel planar surfaces;

wherein said parallel curved surfaces of said first slot and said cylindrical curved surface of said second slot in each bracket are respectively curved to match the predetermined curvature of said arch wire so as to provide easy reception of said arch wire into that slot whose orientation best allows application of said corrective force to said tooth to which said bracket is attached.

10. An orthodontic appliance according to claim 9, wherein:
said parallel curved surfaces of said first slot are so arranged as to each be generated by a straight line generatrix moved substantially in parallel to an end surface of said bracket with which said bracket is attached to a tooth.

11. An orthodontic appliance according to claim 9, wherein:
said parallel curved surfaces of said first slot are so arranged as to each be generated by a straight line generatrix moved with a constant inclination relative to an end surface of said bracket with which said bracket is attached to a tooth.

* * * * *